United States Patent [19]

Howarth

[11] 4,104,028
[45] Aug. 1, 1978

[54] METHOD OF TITRATING LIQUOR

[75] Inventor: John Joseph Howarth, Monte Sereno, Calif.

[73] Assignee: Measurex Corporation, Cupertino, Calif.

[21] Appl. No.: 774,157

[22] Filed: Mar. 3, 1977

Related U.S. Application Data

[63] Continuation-in-part of Ser. No. 629,859, Nov. 7, 1975, Pat. No. 4,012,197.

[51] Int. Cl.² .............................................. G01N 27/10
[52] U.S. Cl. .................. 23/230 R; 23/230 A; 23/253 R; 204/1 T
[58] Field of Search .............. 23/230 R, 253 R, 230 A, 23/253 A; 204/1 T, 195 T

[56] References Cited

U.S. PATENT DOCUMENTS

| 2,977,199 | 3/1961 | Quittner | 23/230 R |
| 2,989,377 | 6/1961 | Leisey | 23/230 R |
| 3,160,477 | 12/1964 | Wasilewski | 23/253 R |
| 3,290,116 | 12/1966 | Carroll | 23/230 R |
| 3,308,041 | 3/1967 | Strickler | 23/230 R |
| 3,625,655 | 12/1971 | Culp et al. | 23/253 A |
| 3,888,726 | 6/1975 | Hultman | 23/230 R |
| 3,904,370 | 9/1975 | Robison | 23/230 A |
| 3,950,137 | 4/1976 | Larson et al. | 23/253 R |

OTHER PUBLICATIONS

Quesinberry, "Automated Analysis of Kraft Liquors for Effective alkali," TAPPI, Oct. 1968, vol. 51, No. 10, pp. 40A–43A.

Primary Examiner—R.E. Serwin
Attorney, Agent, or Firm—Ronald L. Yin

[57] ABSTRACT

A method of titrating liquor from a digester comprises removing a portion of the liquor into a sample vessel and using carbon dioxide as a titrant to determine the alkalinity of the liquor.

6 Claims, 5 Drawing Figures

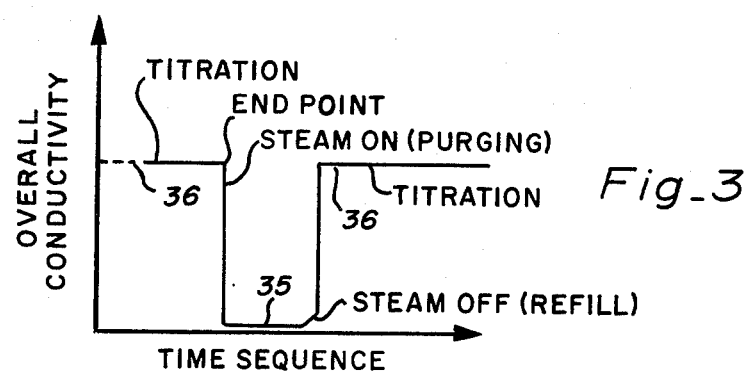
Fig_3
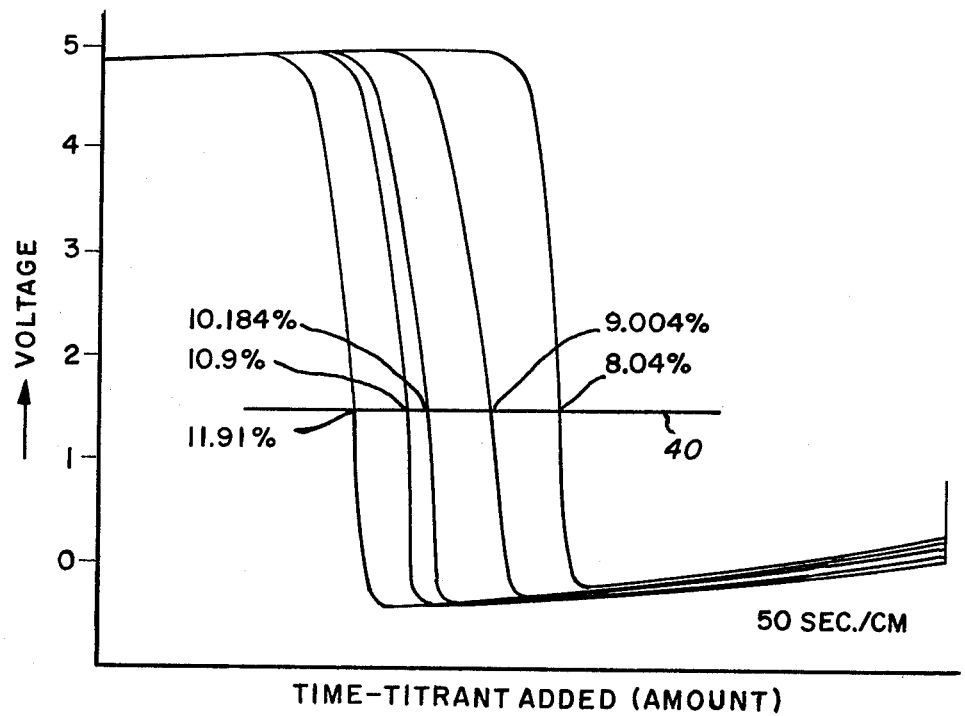
Fig_4
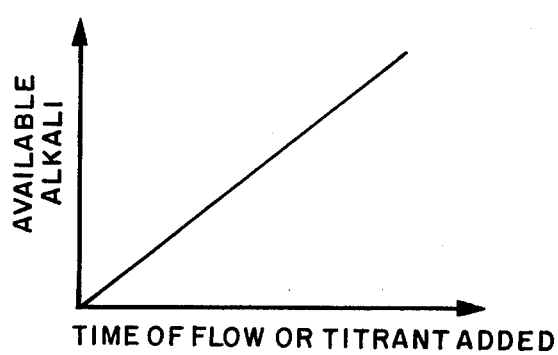
Fig_5

METHOD OF TITRATING LIQUOR

BACKGROUND OF THE INVENTION

This application is a continuation-in-part of a copending application Ser. No. 629,859 filed on Nov. 7, 1975 now U.S. Pat. No. 4,012,197 by the present inventor and assigned to the same assignee.

The present invention is directed to a titration method and more specifically to a method of measuring the available alkali in a Kamyr or batch digester being used for processing paper pulp.

As stated in a paper entitled "Computer Control in Pulp and Paper 1961–1969" by Donald B. Brewster and Andrew K. Bjerring in the Proceedings of the IEEE, Volume 58, No. 1, Jan. 1970, page 51, "at the present time there is no effective commercial on-line instrument available for measuring K number" (in a Kamyr digester). "Manual tests on samples taken from the blow line or washer (of the digester) are performed, usually once per hour." The purpose of the pulp digester is, of course, to convert the wood into fiber. This is achieved in the digester by treating the wood chips with a white liquor which consists of a solution of sodium sulfide and sodium hydroxide. Both high heat and pressure are present in the digester to provide delignification. Lignin accounts for about 30% of the wood and it is removed to allow easy separation and bleaching of the cellulose fibers. The usual measure of the extent of delignification is the "K number"; the lower the K number, the lower the residual lignin. An alternate to the measure of K number is the measure of the alkalinity of the liquor in the digester indicating the extent of the reaction between the alkali and the lignin.

With an on-line measurement of K number of alkalinity much better control of the digester is possible. At the present time as discussed on page 55 of the Brewster article the most feasible method of K number regulation is to use feedforward control and keep the following five factors constant: liquor to wood ratio, temperature, residence time and chip level control. In order to stabilize this feedforward control, the 1 hour sample of the blow line is utilized as a feedback control. It is apparent that because of the long time delay involved to obtain a K number sample the entire control scheme is unsatisfactory. To remedy the foregoing, a Swedish company under the name ASEA utilizes an on-site titrator to determine alkalinity with a "mechanical man" to obtain the sample. This is not an effective on-line measurement since the time required is over ten minutes. Also the moving parts of the "mechanical man", especially under the high pressure and temperature conditions in a typical digester, make the design, operation and maintenance of such a system impractical.

Moreover, the selection of a titrant for on-line measurement of liquor must be chosen with care. The handling of the titrant, the by-product of the titration process and the physical constraint of being on-line are all factors which must be considered. Heretofore, the titrant used for titrating liquor has been hydrochloric acid. However, because no effective on-line titration apparatus has been successfully developed, hydrochloric acid has been successfully used only for off-line titration. As an on-line titrant, hydrochloric acid would suffer from the disadvantage of corrosion. As an acid, it would be hard to handle. More importantly, the reaction of hydrochloric acid and liquor produces sodium chloride, which is not naturally occuring in the digester. As an on-line process, the sodium chloride would present corrosion problems to the digester. Finally, as a liquid, the hydrochloric acid would add volume to a sample vessel in an on-line apparatus. This would give rise to an error in measuring the amount of alkali in a given volume.

SUMMARY OF THE INVENTION

A method of titrating liquor from a digester comprises removing a portion of the liquor into a sample vessel and introducing carbon dioxide into the vessel as the titrant.

BRIEF DESCRIPTION OF THE DRAWINGS

FIG. 3 is a time sequence diagram useful in understanding the operation of the method of the present invention;

FIG. 4 is a graph useful in understanding the operation of the method of the present invention;

FIG. 5 is a graph illustrating the operation of the invention.

DETAILED DESCRIPTION OF THE DRAWINGS

Figure 1:
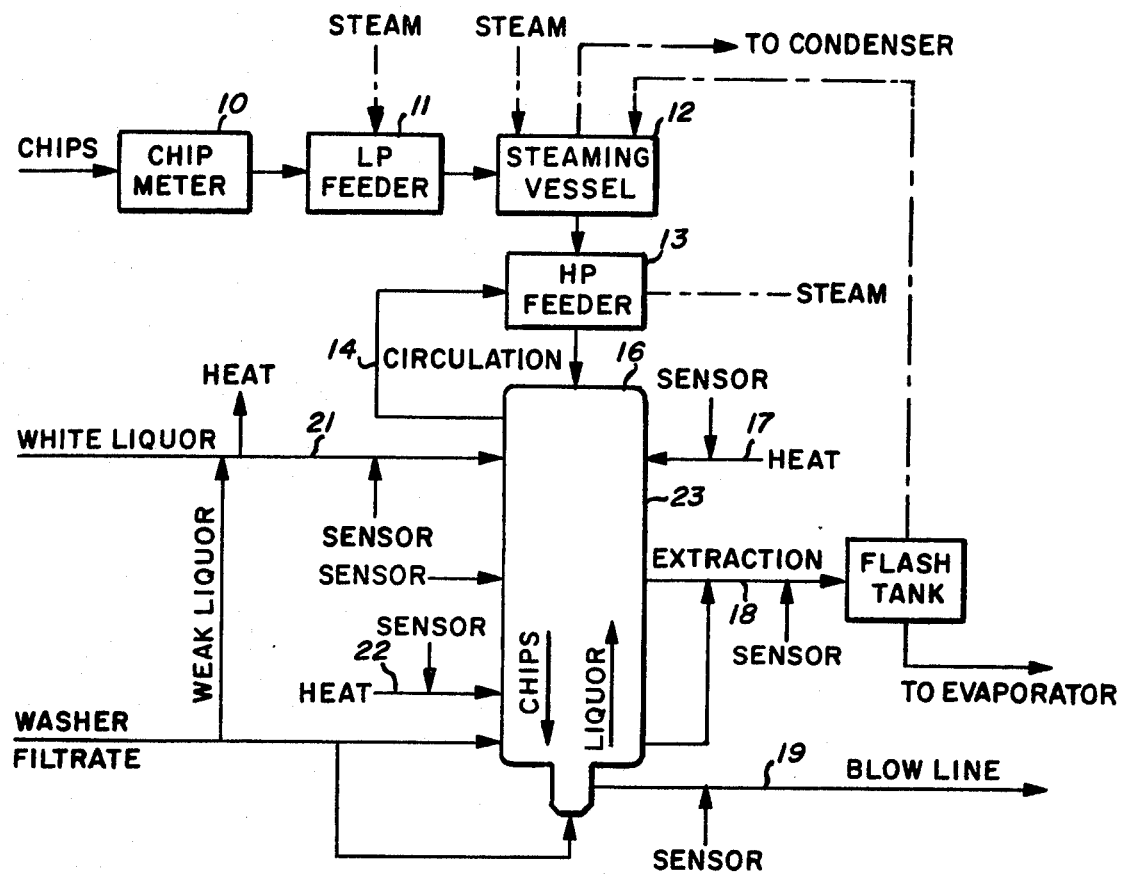
FIG. 1 is a block diagram of a digester.

FIG. 1 illustrates a Kamyr digester in schematic form. The digester is well-known in the art except for the technique of sensing the alkali concentration at the various levels. In general, in operation chips are metered volumetrically by a chip meter 10 and a low pressure feeder 11 into a steaming vessel 12 whose prime function is to drive off air, the presence of which would inhibit liquor penetration. The chips are then mixed with circulating liquor from the circulating line 14 in high pressure feeder 13 and forced into the top separator section of the main digester container 16. In the top separator excess liquor is separated, mixed with the white liquor makeup, and recirculated. The chips settle onto the top of the chip-liquor mass already in the impregnation zone of the digester. As discussed above, white liquor consists of a solution of sodium sulfide and sodium hydroxide.

After about forty minutes residence in the digester heat is added at point 17 by circulating a portion of the liquor through heating coils. This raises the temperature so that delignification occurs. The cooking zone extends down to the extraction point 18 which extracts the spent liquor (now known as black liquor) for recovery in a manner well-known in the art. Pulp is removed from the bottom of the digester about four hours after it leaves the cooking zone. Such removal is accomplished via the blow line 19. White liquor is also added at the line 21 along with heat. Finally heat is added via the recirculating line 22.

Figure 2:
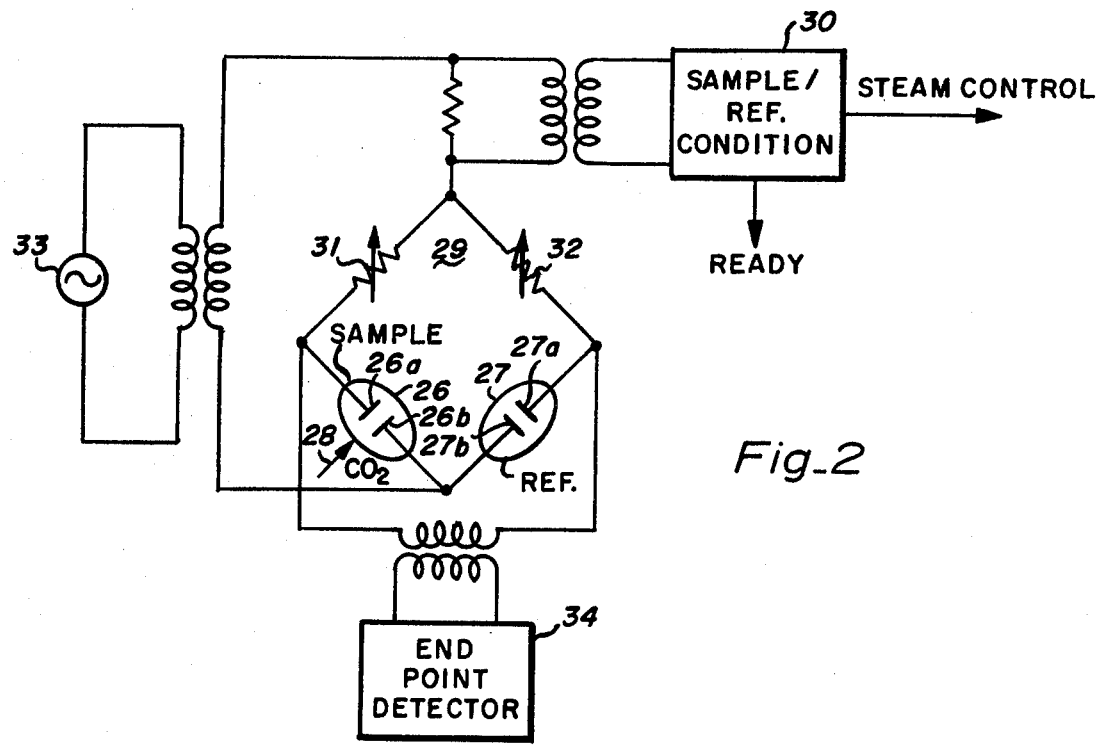
FIG. 2 is a simplified electrical schematic of an apparatus embodying the method of the present invention.

A sensor to detect the available alkali may be located at several locations in the digester. This includes the white liquor input line 21, a side wall portion 23 of the digester, the heat input 22, the heat input 17, extraction output 18 and the blow line 19. Also, the sensor may be on-line or off-line. Depending on the preferred control scheme one or more of the sensors may be utilized for appropriate feedback control. Thus, direct control of K number may be effected. In an on-line configuration a typical sensor is illustrated in schematic form in FIG. 2 and includes a sample vessel 26 and a reference vessel 27 which are both suspended with a vertical orientation inside a contained volume associated with the digester. It may either be in the side wall 23 or in one of the many recirculating pipe lines shown. The sensor may also be on-line but outside the digester with input lines from the digester to it. Vessels 26 and 27 also include the associated electrodes 27a, b and 26a, b. These electrodes, as will be apparent from the discussion below, measure the change in conductivity of the liquid being measured when a titrant is added to the liquid which is more scientifically termed an analyte. Titration is accomplished by the addition of carbon dioxide by a line 28 to the sample vessel 26. The electrodes and their associated vessels are part of an overall Wheatstone bridge 29 which includes the adjustable balancing resistors 31 and 32. A generator 33 drives the bridge. An end point detector 34 is connected to the bridge to provide a signal indicative of the available alkali in the sample vessel. In practice detector 34 would include an emplifier connected to a minicomputer.

The use of a separate reference vessel (which, of course, has no titrant added to it) insures that chemical changes which occur in the process during measurement are compensated for and also provides a bridge type measurement which is inherently highly accurate. However, in many applications this may not be necessary and the reference vessel may be replaced by a simple resistor.

Referring now also to FIG. 3 the overall conductivity of bridge 29 is sensed by a sample/reference condition unit 30. When neither vessel 26 or 27 contains any liquid a low conductivity condition (level 35) occurs indicating that the vessels have been purged. However, after refilling a normal conductivity level 36 is present. These levels, as will be discussed below, are useful for sequencing purposes.

FIG. 4 illustrates typical test results with different percentages of alkalinity in a constant volume. The horizontal axis is time or amount of titrant added (since the carbon dioxide flow is constant) versus the output voltage to end point detector 34 of FIG. 2. The horizontal line 40 is a voltage level which establishes the end point at which the titrant balances the analyte and where an abrupt change in conductivity takes place. This change takes place when all of the available sodium hydroxide has reacted with the injected carbon dioxide to form sodium carbonate. The percentages of alkalinity are illustrated on the drawing of FIG. 4. Line 40 would normally be obtained either by an empirical selection of a voltage level and a particular environment or determining the midpoint between the maximum and minimum of the curves. FIG. 5 illustrates the substantially direct relationship between the amount of titrant added and the percentage of alkalinity or available alkali. Assuming a constant flow of titrant or carbon dioxide the time interval from the start of injection of the titrant to end point is therefore a measure of the concentration of the analyte. Thus the only electrical measurement necessary is the abrupt change in conductivity which is inherently highly immune to error; for example, inert material in the sample, electrode fouling, or drifts in associated electronics. The detection of the end point of the titration may also be accomplished by a temperature probe. As it is well known, in most chemical reactions, heat is liberated. In the instant case, the titration of liquor also produces heat. The detection of an abrupt change in temperature rise would also signify the end point of the titration. Again, measurement of the time interval from the start of the injection of the titrant to the end point is a measurement of the amount of titrant introduced, which in turn determines the concentration of the analyte.

The titrant used is carbon dioxide since the reaction of the carbon dioxide with the solution of liquor, which as discussed above consists of sodium hydroxide and sodium sulfide, produces sodium carbonate which is already present in the digester. Thus, there is no contamination of the liquor.

Carbon dioxide as a titrant for on-line measurement has other advantages. In the physical constraint of being on-line it does not add to the volume of the trapped sample. It is very easy to manipulate. Finally, it is inert.

What is claimed is:

1. A method of titrating alkali paper pulp solution comprising the steps of:
    removing a portion of said solution into a sample vessel, said portion having a known volume;
    selecting a physical characteristic of said solution;
    introducing carbon dioxide into the sample vessel;
    monitoring the amount of carbon dioxide introduced; detecting an abrupt change in said physical characteristic of said solution;
    measuring the total amount of carbon dioxide introduced into said sample vessel immediately upon the detection of said abrupt change; and
    calculating the alkalinity of said solution based upon said amount of carbon dioxide measured and said known volume of said portion.

2. The method of claim 1 wherein said carbon dioxide is introduced at a constant rate.

3. The method of claim 2 wherein:
    said monitoring step is determining the amount of time elapsed from the commencement of introduction of carbon dioxide; and
    said measuring step is computing the total amount of carbon dioxide introduced based upon said elapsed time and said rate.

4. The method of claim 3 wherein said sample vessel is on-line.

5. The method of claim 4 wherein said physical characteristic is conductivity.

6. The method of claim 4 wherein said physical characteristic is temperature.

* * * * *